(12) United States Patent
Kurihara

(10) Patent No.: US 10,195,090 B2
(45) Date of Patent: Feb. 5, 2019

(54) ABSORBENT ARTICLE

(71) Applicant: DAIO PAPER CORPORATION, Ehime (JP)

(72) Inventor: Ryoko Kurihara, Tochigi (JP)

(73) Assignee: DAIO PAPER CORPORATION, Ehime (JP)

(*) Notice: Subject to any disclaimer, the term of this patent is extended or adjusted under 35 U.S.C. 154(b) by 212 days.

(21) Appl. No.: 15/108,621

(22) PCT Filed: Jan. 5, 2015

(86) PCT No.: PCT/JP2015/050005
§ 371 (c)(1),
(2) Date: Jun. 28, 2016

(87) PCT Pub. No.: WO2015/105061
PCT Pub. Date: Jul. 16, 2015

(65) Prior Publication Data
US 2016/0317365 A1    Nov. 3, 2016

(30) Foreign Application Priority Data

Jan. 10, 2014 (JP) .................... 2014-003126
Jun. 13, 2014 (JP) .................... 2014-122038

(51) Int. Cl.
*A61F 13/15* (2006.01)
*A61F 13/511* (2006.01)
(Continued)

(52) U.S. Cl.
CPC .. *A61F 13/51108* (2013.01); *A61F 13/15707* (2013.01); *A61F 13/4756* (2013.01); *A61F 13/536* (2013.01)

(58) Field of Classification Search
CPC .......... A61F 13/51108; A61F 13/15707; A61F 13/4756; A61F 13/536; A61F 13/58;
(Continued)

(56) References Cited

U.S. PATENT DOCUMENTS

| 2003/0078553 | A1 | 4/2003 | Wada et al. |
| 2006/0116652 | A1* | 6/2006 | Miura ............... A61F 13/15203 604/380 |
| 2006/0116653 | A1* | 6/2006 | Munakata ........... A61F 13/4702 604/380 |
| 2006/0276767 | A1* | 12/2006 | Ueminami .......... A61F 13/4702 604/385.31 |

(Continued)

FOREIGN PATENT DOCUMENTS

| EP | 2277482 | * | 1/2011 | ........... A61F 13/534 |
| EP | 2281536 | | 2/2011 | |

(Continued)

OTHER PUBLICATIONS

International Search Report dated Mar. 17, 2015.

*Primary Examiner* — Jacqueline Stephens
(74) *Attorney, Agent, or Firm* — IPUSA, PLLC

(57) ABSTRACT

An absorbent article includes an absorbent body provided between a liquid permeable topsheet and a backsheet; and embosses formed at both sides of the liquid permeable topsheet, wherein each of the embosses includes a body fluid expelling part emboss formed at an area corresponding to a body fluid expelling part along a longitudinal direction of the absorbent article, and is constituted of a shaped line protruding outward in a width direction of the absorbent article, longitudinal direction embosses formed at front and rear of the body fluid expelling part emboss along the longitudinal direction of the absorbent article, respectively, and inclined embosses extending from outer end portions of the longitudinal direction embosses, respectively, and being inclined toward a center side in the width direction of the (Continued)

absorbent article, and wherein end portions of the right and left inclined embosses are spaced apart from each other in the width direction.

13 Claims, 9 Drawing Sheets

(51) Int. Cl.
*A61F 13/475* (2006.01)
*A61F 13/536* (2006.01)

(58) Field of Classification Search
CPC .......... A61F 13/15764; A61F 13/15642; A61F 13/15406; A61F 13/49015; A61F 13/532; A61F 13/587
USPC ............................ 604/378, 379, 380, 385.01
See application file for complete search history.

(56) References Cited

U.S. PATENT DOCUMENTS

| | | | | |
|---|---|---|---|---|
| 2011/0130737 A1* | 6/2011 | Sagisaka | ............. | A61F 13/4704 604/380 |
| 2011/0251575 A1* | 10/2011 | Kuroda | ............... | A61F 13/4704 604/380 |
| 2011/0288514 A1* | 11/2011 | Kuroda | ............... | A61F 13/4704 604/380 |
| 2012/0095424 A1 | 4/2012 | Komatsu et al. | | |

FOREIGN PATENT DOCUMENTS

| | | |
|---|---|---|
| EP | 2612636 | 7/2013 |
| JP | 3971150 | 9/2007 |
| JP | 2010-234031 | 10/2010 |
| JP | 2013-176509 | 9/2013 |

* cited by examiner

ABSORBENT ARTICLE

BACKGROUND OF THE INVENTION

1. Field of the Invention

The present invention relates to an absorbent article such as a sanitary napkin, a panty liner, an incontinence pad or the like for absorbing menstrual blood, vaginal secretions or the like, and more specifically, to an absorbent article including a scale function by which the absorbed liquid amount is visible.

2. Description of the Related Art

Conventionally, as absorbent articles such as panty liners, sanitary napkins, incontinence pads or the like, a structure is known in which an absorbent body made of cellulose wadding, such as crushed pulp or the like, is provided between a liquid impermeable backsheet, such as a polyethylene sheet, a polyethylene sheet laminate non-woven-fabric or the like, and a liquid permeable topsheet, such as a non-woven-fabric, a liquid permeable plastic sheet or the like.

After various improvement on such kinds of absorbent articles, an absorbent article is known in which linear embosses are provided at a surface side of the liquid permeable topsheet for various purposes. For example, in the following Patent Document 1, an absorbent article is disclosed in which a reference mark is provided at a surface of a liquid receiving part for confirming a degree of spread of liquid in the liquid receiving part that is supplied in the liquid receiving part for the purpose of immediately recognizing a degree of absorption and diffusion of the liquid after attaching the absorbent article to facilitate selection of a product thereafter, or the like. The reference mark has a continuous or discontinuous border formed by pressing an absorbent layer and a topsheet, the border is formed to surround predetermined dimension at the surface of the liquid receiving part, and at least two borders are formed such that an outer border is positioned at an outside of an inner border with a space therebetween.

Furthermore, in the following Patent Document 2, an absorbent article is disclosed in which an emboss is constituted of a urine expelling port corresponding emboss, and a front side emboss and a rear side emboss provided at the front and the rear thereof. The urine expelling port corresponding emboss is formed to have a shape protruding outward in a width direction of the absorbent article. At least a portion of each of the front side emboss and the rear side emboss in proximity to the urine expelling port corresponding emboss is formed as a curved line or a straight line having a center of curvature positioned at an outside in the width direction of the absorbent article and having a radius of curvature greater than or equal to the size of the urine expelling port corresponding emboss in the longitudinal direction. With this, the protruding shape of the urine expelling port corresponding emboss becomes more visible compared with the shapes of the front side emboss and the rear side emboss that are positioned at front and rear thereof. Thus, it is described that by attaching the absorbent article such that a portion surrounded by the urine expelling port corresponding emboss is targeted to contact a urine expelling port portion, the absorbent article can be easily attached at an appropriate position of a body.

PATENT DOCUMENTS

Patent Document 1: Japanese Patent No. 3,971,150
Patent Document 2: Japanese Laid-open Patent Publication No. 2013-176509

In order to determine an accurate absorbed amount based on diffused dimension of the body fluid, it is necessary to cause diffusion of the body fluid that is penetrated in the absorbent body, not a spreading of the body fluid flowing at a surface. However, according to the absorbent article disclosed in the above Patent Document 1, because the border constituted of the emboss surrounds the liquid receiving part, the body fluid expelled from a body fluid expelling part is suppressed from diffusing in the absorbent body after being absorbed in the absorbent body due to the emboss. Therefore, it is impossible to observe an accurate absorbed range by the diffusion in the absorbent body.

Further, as the diffusion in the absorbent body is suppressed, there is a problem that the body fluid tends to be trapped at the body fluid expelling part so that stickiness increases to cause discomfort.

On the other hand, according to the absorbent article disclosed in the above described Patent Document 2, although the absorbent article can be attached at an appropriate position of a body by targeting the portion surrounded by the urine expelling port corresponding emboss, as the entirety of the emboss is closed, there is a possibility that the diffusion is suppressed and there is a case that a wearer feels stickiness.

Further, when the embosses formed from a surface side of the permeable topsheet are provided in a separated manner, the force pressing the embosses with respect to a flowing direction is separated and there is a case that the compression force by the embosses is weakened. Further, for the thick absorbent body, as the emboss formed from the surface side of the liquid permeable topsheet is integrally compressing the liquid permeable topsheet, the absorbent body, an encapsulating sheet surrounding the absorbent body and the like, there is a case that floating of the emboss occurs by which a surface material is floated from the absorbent body due to the force generated by returning of the surface material. In particular, as the returning forces are applied from various directions of the emboss, the floating of the emboss is easily generated at an end portion of the emboss.

SUMMARY OF THE INVENTION

Thus, a first problem of the present invention is to provide an absorbent article in which diffusion of body fluid is not suppressed by an emboss, an accurate diffusion status of body fluid is visible, and discomfort due to stickiness does not occur. Further, a second problem is to provide an absorbent article in which floating of an emboss is suppressed as much as possible.

In order to solve the above first problem, as the present invention of claim 1, there is provided an absorbent article including an absorbent body provided between a liquid permeable topsheet and a backsheet; and a pair of embosses formed at both sides of a surface side of the liquid permeable topsheet, wherein each of the embosses includes a body fluid expelling part emboss that is formed at an area corresponding to a body fluid expelling part along a longitudinal direction of the absorbent article, and is constituted of a shaped line protruding outward in a width direction of the absorbent article, longitudinal direction embosses that are formed at the front and the rear of the body fluid expelling part emboss along the longitudinal direction of the absorbent article, respectively, and inclined embosses extending from outer end portions of the longitudinal direction embosses, respectively, and being inclined toward a center side in the width direction of the absorbent article, and wherein end portions of the right and left inclined embosses are spaced apart from each other in the width direction.

In the above invention of claim 1, the emboss includes a body fluid expelling part emboss, longitudinal direction embosses that are formed at the front and the rear of the body fluid expelling part emboss along the longitudinal direction of the absorbent article, respectively, and inclined embosses extending from outer end portions of the longitudinal direction embosses, respectively, and being inclined toward a center side in the width direction of the absorbent article. Thus, using the inclined embosses as a scale, a degree of diffusion of the body fluid in the absorbent body is visible, and this degree of diffusion can be used as a guidepost for selecting the size of the absorbent article that is to be used thereafter.

Further, as end portions of the right and left inclined embosses are spaced apart from each other in the width direction in the absorbent article, spread of the body fluid that diffuses in the absorbent body is not suppressed by the emboss, and an accurate diffusion status in the absorbent body can be observed. Further, as the diffusion of the body fluid is not suppressed, the body fluid does not stay near the body fluid expelling part, and discomfort due to the stickiness can be eased.

As the invention of claim 2, there is provided the absorbent article according to claim 1, wherein two or more pairs of the longitudinal direction embosses are formed at each of the front and rear of the pair of body fluid expelling part embosses with spaced apart from each other in the longitudinal direction, wherein the pairs of longitudinal direction embosses that are adjacent to the pair of body fluid expelling part embosses are connected to the respective body fluid expelling part embosses, and wherein the inclined emboss is formed at the outer end portion of each of the longitudinal direction embosses.

In the above invention of claim 2, by forming two or more pairs of the longitudinal direction embosses at each of front and rear of the pair of body fluid expelling part embosses with spaced apart from each other in the longitudinal direction, and forming the inclined emboss at the outer end portion of each of the longitudinal direction embosses, two or more pairs of the inclined embosses are provided in the longitudinal direction. Thus, these inclined embosses can function more clearly as the scale. Further, by forming the two or more pairs of the longitudinal direction embosses to be spaced apart from each other in the longitudinal direction, flow of the body fluid flowing at a surface from the inner side longitudinal direction emboss to the outer side longitudinal direction emboss can be prevented, and the diffusion status of the body fluid penetrated in the absorbent body, not the diffusing of the body fluid flowing at the surface, can be observed.

Further, as each of the longitudinal direction embosses adjacent to the body fluid expelling part emboss is connected to that body fluid expelling part emboss, the body fluid can move from the body fluid expelling part emboss to the longitudinal direction emboss without the occurrence of side leakage.

In order to solve the above second problem, as the present invention of claim 3, there is provided the absorbent article according to claim 1, wherein two or more pairs of the longitudinal direction embosses are formed at each of the front and the rear of the pair of body fluid expelling part embosses, wherein the pairs of longitudinal direction embosses that are adjacent to the pair of body fluid expelling part embosses are connected to the respective body fluid expelling part embosses, wherein the inclined emboss is formed at the outer end portion of each of the longitudinal direction embosses, and wherein each of the longitudinal direction embosses adjacent to the inclined emboss at its outer side is connected to the respective inclined emboss.

In the above invention of claim 3, two or more pairs of the longitudinal direction embosses are formed at each of front and rear of the pair of body fluid expelling part embosses, and each of the longitudinal direction embosses that is adjacent to the inclined emboss at its outer side is connected to the respective inclined emboss. This means that the body fluid expelling part emboss, the longitudinal direction embosses and the inclined embosses are formed by a continuous line without being separated. With this, as end portions of the emboss are decreased compared with a case when the embossed lines are separately formed, the force pressing the emboss becomes constant and floating of the emboss due to a returning force of a surface material can be prevented.

As the present invention of claim 4, there is provided the absorbent article according to claim 2 or 3, wherein each of the longitudinal direction embosses provided relatively outer side is provided at a position that does not match an extension line extending from the adjacent longitudinal direction emboss that is at an inner side thereof.

In the above invention of claim 4, by providing each of the longitudinal direction embosses, that is provided relatively outer side, at a position that does not match an extension line extending from the adjacent longitudinal direction emboss that is at an inner side thereof, continuous flow from the inner side longitudinal direction emboss to the outer side longitudinal direction emboss can be surely prevented.

As the present invention of claim 5, there is provided the absorbent article according to one of claims 2 to 4, wherein each of the longitudinal direction embosses, that is provided relatively outer side, is provided inside of an extension line extending from the adjacent longitudinal direction emboss that is at an inner side thereof.

In the above invention of claim 5, by providing each of the longitudinal direction embosses, that is provided relatively outer side, inside of an extension line extending from the adjacent longitudinal direction emboss that is at an inner side thereof, spread of the body fluid in the width direction can be suppressed.

As the present invention of claim 6, there is provided the absorbent article according to one of claims 1 to 5, wherein each of the longitudinal direction embosses that is adjacent to the body fluid expelling part emboss is formed along a single arc-shaped curve that protrudes inward in the width direction of the absorbent article, and wherein a position of narrowest portions at which the distance between the right and left arc-shaped curves becomes the minimum, and a position of maximum protruding portions at which an outward protruding width in the width direction of the right and left body fluid expelling part embosses match or are in proximity to each other.

In the above invention of claim 6, by forming each of the longitudinal direction embosses that is adjacent to the body fluid expelling part emboss is along a single arc-shaped curve that protrudes inward in the width direction of the absorbent article, and making a position of narrowest portions at which the distance between the right and left arc-shaped curves becomes the minimum, and a position of maximum protruding portions at which an outward protruding width in the width direction of the right and left body fluid expelling part embosses match or being in proximity to each other, the absorbent article can be attached at the appropriate position when attaching it such that a body fluid expelling part is aligned at a center portion of the protruding shapes of the body fluid expelling part embosses.

As the present invention of claim 7, there is provided the absorbent article according to one of claims 2 to 6, wherein, among the inclined embosses, each of the inclined embosses that is formed nearest to the body fluid expelling part emboss is formed such that an angle α with respect to a width direction line of the absorbent article is less than or equal to 45°, and each of the inclined embosses that is formed further outer side is formed such that an angle with respect to the width direction line of the absorbent article is less than or equal to 60°.

In the above invention of claim 7, among the inclined embosses, by forming each of the inclined embosses that is formed nearest to the body fluid expelling part emboss such that an angle α with respect to a width direction line of the absorbent article, and forming each of the inclined embosses that is formed further outer side is formed such that an angle with respect to the width direction line of the absorbent article to be predetermined angles, respectively, the body fluid that flows along the emboss can be guided inside and the body fluid that diffuses in the absorbent body can be guided inside.

As the present invention of claim 8, there is provided the absorbent article according to one of claims 1 to 7, wherein the distance between end portions of the right and left inclined embosses is one to three times of the length of the respective inclined emboss in the width direction of the absorbent article.

In the above invention of claim 8, by setting the distance between end portions of the right and left inclined embosses to be one to three times of the length of the respective inclined emboss in the width direction of the absorbent article, the body fluid can be diffused from the body fluid expelling part in front and rear directions of the absorbent body, without suppressing natural diffusion of the body fluid in the front and rear directions, discomfort due to the stickiness of the body fluid expelling part can be suppressed.

As the present invention of claim 9, there is provided the absorbent article according to one of claims 2 to 8, wherein each of the longitudinal direction embosses is formed to have an inclined angle such that its outer side is inclined outward in the width direction with respect to a longitudinal direction line of the absorbent article, and wherein the inclined angle of each of the longitudinal direction embosses that is provided relatively outer side is set to be larger than the inclined angle of the adjacent longitudinal direction emboss that is at an inner side thereof.

In the above invention of claim 9, as the inclined angle of each of the longitudinal direction embosses that is provided relatively outer side is set to be larger than the inclined angle of the adjacent longitudinal direction emboss that is at an inner side thereof, even when two or more pairs of the longitudinal direction embosses are provided each of front and rear of the pair of body fluid expelling part embosses, and the body fluid expelling part emboss, the longitudinal direction embosses and the inclined embosses are formed by a continuous line, the diffusion of the body fluid that flows along the embossed groove is suppressed at the outer side longitudinal direction emboss whose inclined angle is larger, and the diffusion status of the body fluid absorbed in the absorbent body can be easily observed.

As the present invention of claim 10, there is provided the absorbent article according to one of claims 1 to 9, wherein the groove width of each of the inclined embosses is set larger than the groove width of each of the longitudinal direction embosses.

In the above invention according to claim 10, by setting the groove width of each of the inclined embosses to be larger than the groove width of each of the longitudinal direction embosses, even when two or more pairs of the longitudinal direction embosses are provided each of front and rear of the pair of body fluid expelling part embosses, and the body fluid expelling part emboss, the longitudinal direction embosses and the inclined embosses are formed by a continuous line, the body fluid is temporarily trapped at each of the inclined embosses, and the diffusion of the body fluid along the embossed groove is suppressed. Thus, the diffusion status of the body fluid absorbed in the absorbent body can be easily observed.

As described above in detail, according to the present invention, an absorbent article can be provided in which diffusion of body fluid is not suppressed by an emboss, an accurate diffusion status of body fluid is visible, and discomfort due to stickiness does not occur. Further, an absorbent article is provided in which floating of an emboss is suppressed as much as possible.

DETAILED DESCRIPTION OF THE PREFERRED EMBODIMENTS

First Embodiment

Figure 1:
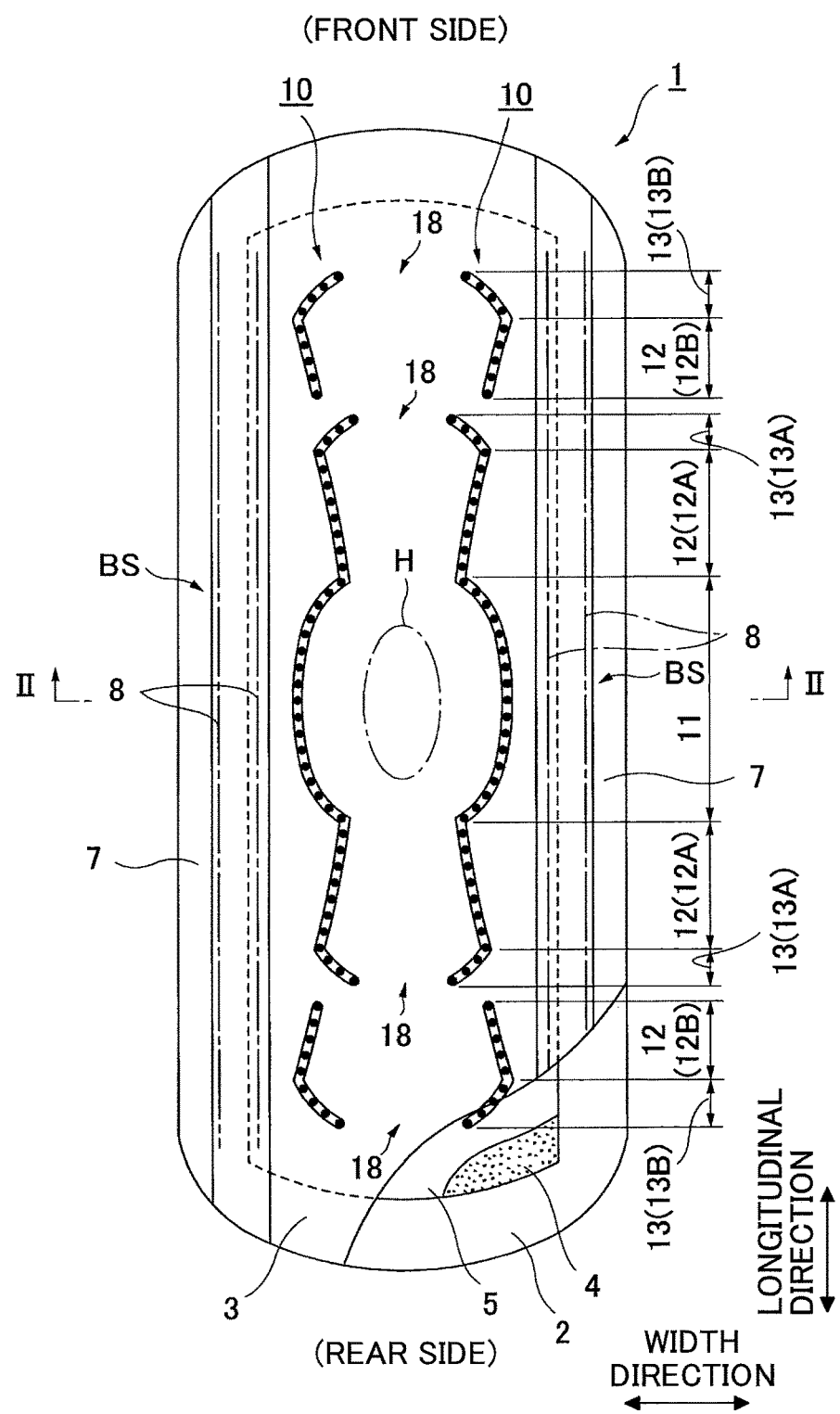
FIG. 1 is a partially broken development view of an incontinence pad 1 of a first embodiment of the invention.
Figure 2:
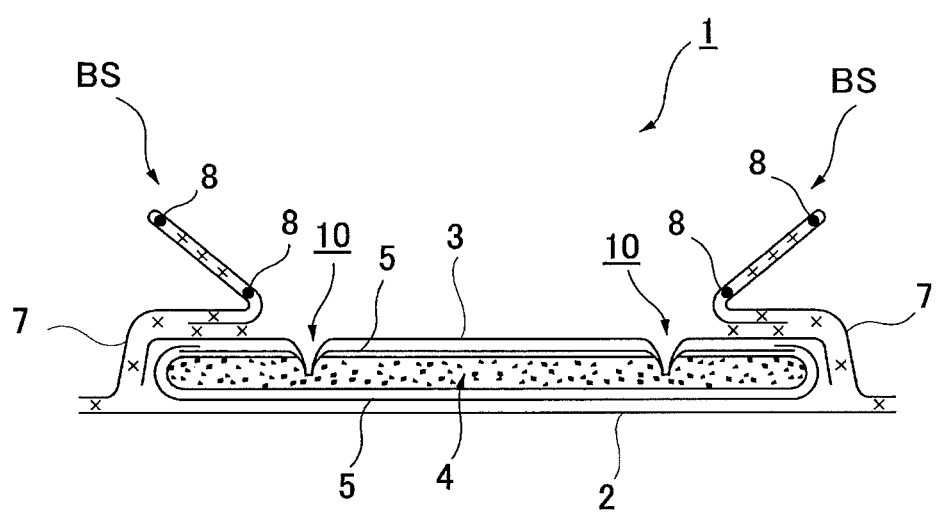
FIG. 2 is a cross-sectional view taken along a II-II line of FIG. 1.

In the following, embodiments of the present invention are described with reference to the accompanying drawings. As illustrated in FIG. 1 and FIG. 2, an incontinence pad 1 of the invention is mainly constituted of a liquid impermeable backsheet 2 made of a polyethylene sheet or the like, a liquid permeable topsheet 3 that allows urine or the like to rapidly permeate, an absorbent body 4 made of cotton-like pulp, synthetic pulp or the like and provided between these sheets 2 and 3, an encapsulating sheet 5, made of a crepe paper, a non-woven-fabric or the like, that surrounds the absorbent body 4 for retaining the shape and improving the diffusion of the absorbent body 4, and non-woven fabric sides 7, 7 forming a pair of standing gathers BS, BS in a lateral direction that protrude toward a skin side in a predetermined zone including at least a body fluid expelling area H in a longitudinal direction while standing from approximately side edge parts of the absorbent body 4. Around the absorbent body 4, outer end portions of the liquid impermeable backsheet 2 and the liquid permeable topsheet 3 are bonded with an adhesive, such as a hot-melt adhesive or an adhesive means such as a heat seal or the like, at end portions in a longitudinal direction, and the liquid impermeable backsheet 2 laterally protruding from the absorbent body 4 and the side non-woven-fabrics 7 are bonded with the adhesive, such as the hot-melt adhesive or the adhesive means such as the heat seal or the like at end portions, on both sides. Further, in accordance with necessity, a hydrophilic second sheet (not illustrated in the drawings) may be provided between the liquid permeable topsheet 3 and the absorbent body 4.

Hereinafter, the structure of the incontinence pad 1 is further described in more detail. A sheet material having at least water shielding properties such as polyethylene, polypropylene or the like is used for the liquid impermeable backsheet 2. In addition to this, a non-woven fabric sheet may be used after ensuring substantial impermeability by providing interposing a waterproof film (in this case, the liquid impermeable backsheet is composed of the waterproof film and the non-woven fabric sheet). In recent years, a material having moisture permeability is often preferably used to prevent sweating. A microporous sheet obtained by forming a sheet by melting and kneading inorganic filler in olefin series resin such as polyethylene, polypropylene or the like and then extruding the sheet in one axial direction or two axial directions, is preferably used as the waterproof and moisture permeable sheet material.

Next, a perforated or imperforate non-woven fabric or a porous plastic sheet is preferably used for the liquid permeable topsheet 3. For example, a regenerated fiber such as rayon, cupra (cuprammonium rayon) or the like, and a natural fiber such as cotton or the like, may be used as a material fiber forming the non-woven fabric in addition to a synthetic fiber including an olefin series such as polyethylene, polypropylene or the like, a polyester series, a polyamide series or the like. As the non-woven fabric, a non-woven fabric obtained by a proper processing method such as a spun lace method, a spun bond method, a thermal bond method, a melt blown method, a needle punch method or the like, may be used. Among these processing methods, the spun lace method is superior in terms of great flexibility and drape properties, and the thermal bond method is superior in terms of bulkiness and softness.

The absorbent body 4 is, for example, constituted of an absorbable fiber such as a fluff pulp or the like and superabsorbent polymers, and is formed into an approximately oval shape extending long in a longitudinal direction of the pad in a planar shape in the illustrated example. The superabsorbent polymers are, for example, formed into granular powders, and are diffused and mixed into the pulp forming the absorbent body 4.

Chemical pulp obtained from wood, a cellulose fiber such as dissolving pulp or the like, and an artificial cellulose fiber such as rayon, acetate or the like, are cited as examples available for the pulp, and softwood pulp having a fiber length longer than that of hardwood pulp is preferably used in terms of function and price. In this incontinence pad 1, as the absorbent body 4 is surrounded by the encapsulating sheet 5, as a result, the encapsulating sheet 5 is provided between the liquid permeable topsheet 3 and the absorbent body 4. Thus, the encapsulating sheet having excellent absorbability serves to rapidly distribute the body fluid and to prevent urine and the like from flowing back. The fabric weight per unit area of the pulp is preferably set in a range of 100 $g/m^2$ to 600 $g/m^2$, and further preferably set in a range of 150 $g/m^2$ to 400 $g/m^2$.

For example, a cross-linking polyacrylate, a self-cross-linking polyacrylate, a saponified substance of a cross-linking copolymer of acrylic acid ester and vinyl acetate, a cross-linking substance of a copolymer of isobutylene and maleic anhydride, a cross-linking polysulfonate, and a partially cross-linking substance of a water swellable polymer such as polyethylene oxide, polyacrylamide or the like are cited as examples of the superabsorbent polymer. Among these examples, a substance of acryl acid or an acrylate-based substance having a large amount of water absorption and a high absorption speed is preferable. The water-absorbing power (water-absorbing ratio) and the water absorption speed of the superabsorbent polymer having the above-mentioned water absorption performance can be adjusted by adjusting a cross-linking density and a cross-linking density gradient in its manufacturing process. The fabric weight per unit area of the polymer is preferably set in a range of 60 $g/m^2$ to 400 $g/m^2$, and further preferably set in a range of 100 $g/m^2$ to 300 $g/m^2$ for providing a predetermined absorbing ability to a body fluid expelling part and its vicinity.

Moreover, a synthetic fiber may be mixed into the absorbent body 4. For example, a polyolefin series such as polyethylene, polypropylene or the like, a polyester series such as polyethylene terephthalate, polybutylene terephthalate or the like, and a polyamide series such as nylon or the like, or a copolymer thereof, or a mixture of two kinds thereof, may be used as the synthetic fiber. Furthermore, a composite fiber such as a core-clad type fiber including a core made of a fiber with a high melting point and a clad made of a fiber with a low melting point, a side-by-side type fiber, a division type or the like, may be also used. When the synthetic fiber is made of a hydrophobic fiber, it is preferable to treat a surface of the synthetic fiber with a hydrophilic agent so as to have hydrophilic properties to the body fluid.

A middle-high portion in which the amount of pulp or polymer is greater than that in the absorbent body base portion or a polymer sheet may be partially provided in the absorbent body 4. When forming the middle-high portion, it is preferable that an emboss 10, which will be described later in detail, is formed outside of the middle-high portion.

On both sides of a surface side of the present incontinence pad 1, the side non-woven fabrics 7, 7 are respectively provided along the longitudinal direction over the entire length of the incontinence pad 1, and outer portions of the side non-woven-fabrics 7, 7 extend laterally while the liquid impermeable backsheet 2 extends laterally. Side flaps are formed by attaching the laterally extended side non-woven-fabric 7 portions to the laterally extended liquid impermeable backsheet 2 portions with the hot-melt adhesive or the like.

Either water-repellent non-woven fabric or hydrophilic non-woven fabric is used as the side non-woven-fabric 7 depending on the desired function. For example, when regarding a function of preventing urine and the like from permeating or of improving a texture as important, it is preferable to use a water-repellent non-woven fabric such as SSMS, SMS or SMMS coated with water-repellent agent and the like of a silicon series, a paraffin series and an alkyl chromic chloride series. When regarding the absorbability of the body fluid as important, it is preferable to use a hydrophilic non-woven fabric obtained by making a swellable or porous synthetic fiber by a method of polymerizing the synthetic fiber in the presence of a compound having a hydrophilic group, for example, an oxidation product of polyethylene glycol, in the manufacture of the synthetic fiber, or a method of treating the surface with a metallic salt such as stannic chloride to partially dissolve the surface to form a porous surface and then to precipitate a metallic hydroxide on the surface, and then providing the hydrophilic property for the synthetic fiber using capillary action. A fiber obtained by processing the natural fiber, the synthetic fiber or the regenerated fiber by a proper processing method is available for the side non-woven-fabric 7.

As illustrated in FIG. 2, an outer side portion of each of the side non-woven-fabrics 7, with respect to a center portion in the width direction, is bonded by an adhesive such as a hot-melt adhesive at a range from an inner side position of the absorbent body 4, slightly passing through a side edge of the absorbent body to an outer edge of the liquid impermeable backsheet 2. Meanwhile, an inner side portion of each of the side non-woven-fabrics 7 is folded in the width direction, and at least a folded front end portion is constituted of double sheets, and at least one, two in the illustrated example, threadlike elastic stretchable members 8, 8, which are fixed at both ends or at arbitrarily selected positions in the longitudinal direction, are provided in the double sheets. The portion folded in the width direction adheres to a lower layer side at front and rear end portions in the longitudinal direction of the napkin. As illustrated in FIG. 2, the standing gathers BS, BS standing toward a front surface side due to contracting effects of the threadlike elastic stretchable members 8, 8 are formed at other center portions in the longitudinal direction of the napkin at which the threadlike elastic stretchable members 8, 8 are provided.

As illustrated in FIG. 1, a pair of embosses 10, 10 that are spaced apart from each other in the lateral direction are formed at a surface side of the liquid permeable topsheet 3. This pair of embosses 10, 10 are formed by integrally pressing the liquid permeable topsheet 3, the encapsulating sheet 5 and the absorbent body 4 by compression from the front surface side of the liquid permeable topsheet 3.

As illustrated in FIG. 1, each of the embosses 10 is constituted of a body fluid expelling part emboss 11, longitudinal direction embosses 12 and inclined embosses 13. For the example illustrated in FIG. 1, the longitudinal direction embosses 12 are constituted of first longitudinal direction embosses 12A formed at body fluid expelling part emboss 11 sides (inner side) and second longitudinal direction embosses 12B that are formed further outward in the longitudinal direction and spaced apart from the first longitudinal direction embosses 12A, respectively. Further, the inclined embosses 13 are constituted of first inclined embosses 13A that extend from outer end portions of the first longitudinal direction embosses 12A and second inclined embosses 13B that extend from outer end portions of the second longitudinal direction embosses 12B, respectively.

The body fluid expelling part embosses 11 are a pair of embossed lines that are spaced apart from each other in the lateral direction and formed at a range including an area overlapping an area corresponding to the body fluid expelling area H in the width direction of the pad. Further, the body fluid expelling part embosses 11 are formed along the longitudinal direction of the incontinence pad 1 and constituted of shaped lines each protruding outward in the width direction of the incontinence pad 1. These body fluid expelling part embosses 11 are provided to prevent the body fluid absorbed in the absorbent body 4 between the right and left body fluid expelling part embosses 11, 11 from diffusing outward in the width direction to cause side leakage and to prevent the body fluid from flowing outsides in the width direction by introducing the body fluid, that is flowing outward from a center portion in the width direction at a front surface, into concave grooves. The right and left body fluid expelling part embosses 11, 11 are independently provided spaced apart from each other in the width direction of the pad. The entirety of each of the body fluid expelling part embosses 11 is formed by a shaped line protruding outward in the width direction in which a center portion in the longitudinal direction is positioned to the outer side in the width direction with respect to both end portions in the longitudinal direction, and is formed in various embodiments such as an arc-shape, an outline of ellipse or the like. It is preferable that the body fluid expelling part emboss 11 is symmetrically formed in front and rear directions with respect to a center portion of the body fluid expelling part emboss 11 in the front and rear directions so that the diffusion of the body fluid in the front and rear directions become the same.

In this specification, "formed along the longitudinal direction of the incontinence pad 1" means that a straight line connecting end portions of the emboss substantially extends along the longitudinal direction of the incontinence pad 1, and includes, in addition to a case in which the straight line is in parallel to a longitudinal direction line, a case in which a difference in angle with respect to the longitudinal direction line is within ±40°. Further, the embossed line is unnecessarily a straight line and may be formed by a curve, a polygonal line, a wavy line or the like.

The longitudinal direction embosses 12 are a pair of embossed lines that are apart from each other in the lateral direction that are formed at front or rear of the body fluid expelling part emboss 11 along the longitudinal direction of the incontinence pad 1. The longitudinal direction embosses 12 are provided to prevent side leakage due to diffusion of the body fluid within the absorbent body in the width direction of the pad, and to guide the body fluid to diffuse in the longitudinal direction of the pad. It is preferable that two or more pairs of the longitudinal direction embosses 12 are formed spaced apart from each other in the longitudinal direction for providing a scale function to the inclined embosses 13, which will be explained later in detail. For the illustrated example, two pairs of the longitudinal direction embosses 12, apart from each other in the longitudinal direction, are formed at each of front and rear of the body fluid expelling part embosses 11, in other words, the first longitudinal direction embosses 12A and the second longitudinal direction embosses 12B are placed in this order from inner side.

It is preferable that the longitudinal direction emboss 12 is constituted of a straight line or a curve with respect to a substantially longitudinal direction of the pad. It is preferable that the longitudinal direction emboss 12 is provided to be inclined with respect to the longitudinal direction line of the pad such that the outer side thereof in the longitudinal direction of the pad is positioned outer side in the width direction of the pad. With this, natural diffusion, by which the body fluid diffused outward from a range surrounded by the body fluid expelling part embosses 11, 11 diffuses outward in the width direction of the pad while flowing outward in the longitudinal direction of the pad, is not blocked and the diffusion of the body fluid proceeds smoothly.

Figure 4:
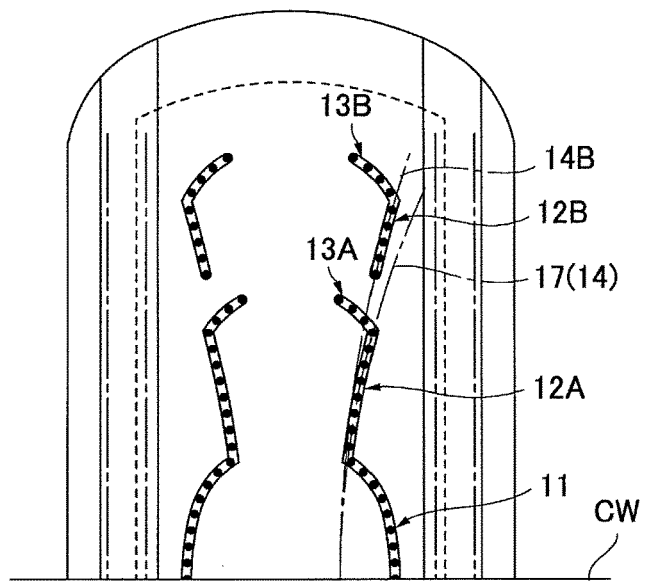
FIG. 4 is a plan view of the incontinence pad 1.

Further, although the longitudinal direction emboss 12 may be constituted of a straight line, as illustrated in FIG. 4, it is preferable that the longitudinal direction emboss 12 is constituted of a curved line that protrudes toward the inner side in the width direction of the pad in order to further smoothly promote diffusion of the body fluid in the absorbent body.

The first longitudinal direction embosses 12A are a pair of embossed lines that are apart from each other in the lateral direction, adjacently placed at each of front and rear of the body fluid expelling part embosses 11, connected to end portions of the body fluid expelling part embosses 11 in the longitudinal direction, and continuously extending from the end portions of the body fluid expelling part embosses 11 in the longitudinal direction, as base points, in the substantially longitudinal direction of the pad.

Figure 3:
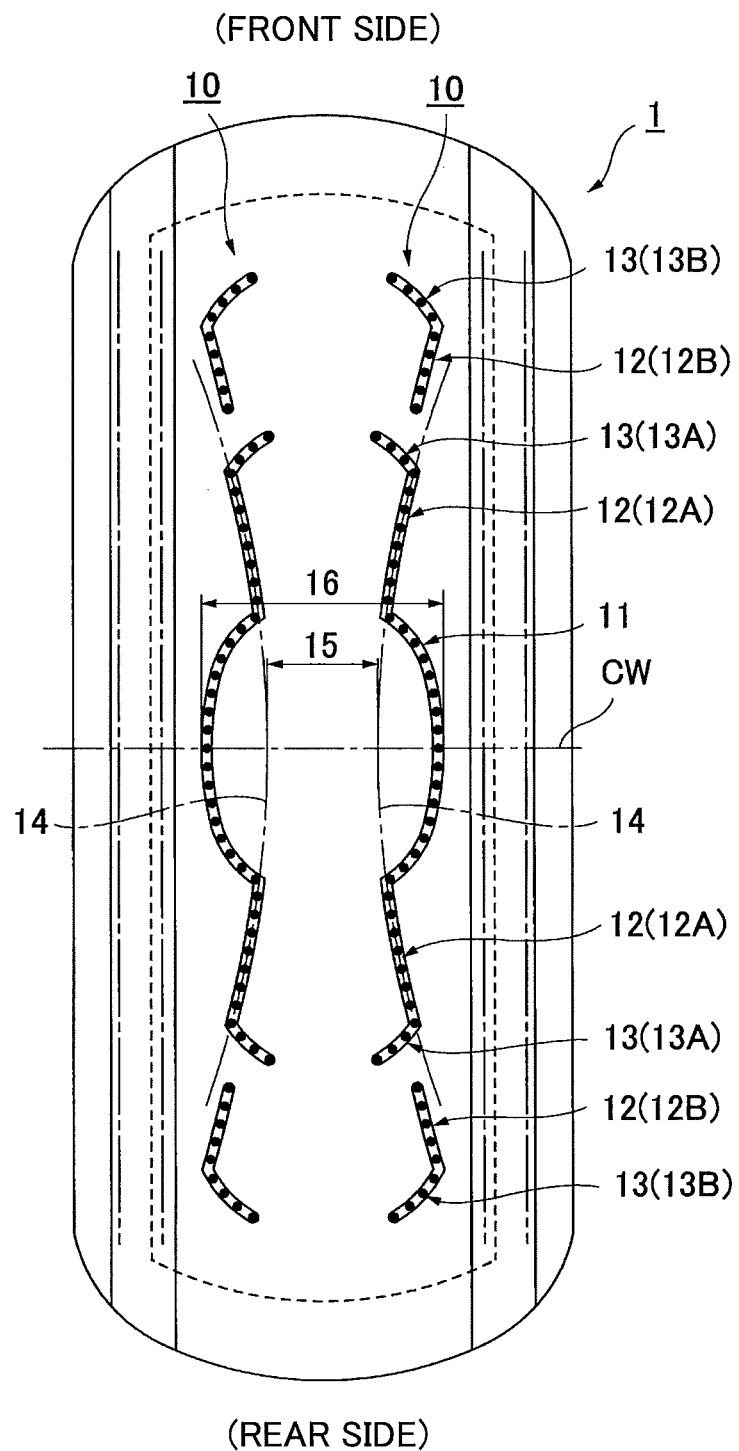
FIG. 3 is a plan view of the incontinence pad 1.

As illustrated in FIG. 3, it is preferable that the first longitudinal direction embosses 12A, 12A continuously formed at the front and the rear of the body fluid expelling part emboss 11, respectively, are formed such that an extension line connecting the first longitudinal direction embosses 12A, 12A extends along a single arc-shaped curve 14 that protrudes inward in the width direction of the incontinence pad 1. By placing on such an arc-shaped curve 14, the body fluid expelling part embosses 11 become more visible compared with the first longitudinal direction embosses 12A, 12A provided at their front and rear sides. Thus, by attaching the incontinence pad 1 such that a portion surrounded by the right and left body fluid expelling part embosses 11, 11 is targeted to contact the body fluid expelling area H, the incontinence pad 1 can be easily attached at an appropriate position of the body. Here, for the example illustrated in FIG. 3, the first longitudinal direction embosses 12A, 12A are symmetrically provided in front and rear directions with respect to a width direction center line CW of the incontinence pad 1 by positioning a center of curvature of the arc-shaped curve 14 on the width direction center line CW.

It is preferable that the first longitudinal direction embosses 12A are placed such that a position of narrowest portions 15 at which the distance between the right and left arc-shaped curves 14, 14 becomes the minimum, and a position of maximum protruding portions 16 at which an outward protruding width in the width direction of the right and left body fluid expelling part embosses 11, 11 match or are in proximity to each other. It is most preferable that the narrowest portions 15 of the arc-shaped curves 14, 14 and the maximum protruding portions 16 of the body fluid expelling part embosses 11, 11 match in the longitudinal direction of the pad, and it is preferable that they are in proximity to each other in the longitudinal direction of the pad (the distance therebetween in the longitudinal direction of the pad is less than or equal to 10 mm). For the illustrated example, the narrowest portions 15 of the arc-shaped curves 14, 14 and the maximum protruding portions 16 of the body fluid expelling part embosses 11, 11 match at the width direction center line CW of the incontinence pad 1. With this, by attaching the incontinence pad 1 such that the body fluid expelling area H matches the center portion of the protruding shape of the body fluid expelling part embosses 11, the incontinence pad 1 can be attached at an appropriate position.

The second longitudinal direction embosses 12B are a pair of embossed lines that are spaced apart from each other in the lateral direction wherein each of which is formed at an outer side of the first longitudinal direction emboss 12A in the longitudinal direction with spaced apart from the first longitudinal direction emboss 12A and the first inclined emboss 13A and is formed along the substantially longitudinal direction of the incontinence pad 1. These second longitudinal direction embosses 12B are provided to guide the body fluid that has diffused outside of the first longitudinal direction embosses 12A in the longitudinal direction. By providing each of the second longitudinal direction embosses 12B at the outer side of the first longitudinal direction emboss 12A in the longitudinal direction with a space, the body fluid that flows along the embossed line of the first longitudinal direction emboss 12A can be prevented from continuously flowing toward the second longitudinal direction emboss 12B, and the diffusion of the body fluid flowing at a surface can be suppressed.

As illustrated in FIG. 4, similar to the first longitudinal direction embosses 12A, it is preferable that the second longitudinal direction emboss 12B is formed on a single arc-shaped curve 14B that protrudes inward in the width direction of the pad. At this time, as the body fluid diffuses slowly at the second longitudinal direction emboss 12B compared with the diffusion of the body fluid at the first longitudinal direction emboss 12A, it is preferable that the radius of curvature 14B that forms the second longitudinal direction emboss 12B is larger than the radius of curvature of the arc-shaped curve 14 that forms the first longitudinal direction emboss 12A.

As illustrated in FIG. 4, it is preferable that the second longitudinal direction emboss 12B is provided at a position that does not match an extension line 17 extending from the embossed line of the first longitudinal direction emboss 12A at outer side. With this, body fluid that flows along the first longitudinal direction emboss 12A does not easily flow into the second longitudinal direction emboss 12B and the diffusion of the body fluid along the embossed grooves can be suppressed. Not matching the extension line 17 of the second longitudinal direction emboss 12B means that it is preferable that the extension line 17 that passes center of the groove width of the first longitudinal direction emboss 12A does not pass through the groove width of the second longitudinal direction emboss 12B, and it is more preferable that the distance between an end portion of the second longitudinal direction emboss 12B and the extension line 17 is greater than the groove width of the second longitudinal direction emboss 12B. The extension line 17 is a line that extends the shape of the first longitudinal direction emboss 12A. For example, when the first longitudinal direction emboss 12A is formed by an arc as the illustrated example, an arc line that extends the arc toward the outer side is the extension line 17.

As illustrated in FIG. 4, it is preferable that the second longitudinal direction emboss 12B is provided at an inner side of the extension line 17 of the first longitudinal direction emboss 12A in the width direction of the pad. With this, the diffusion of the body fluid in the width direction of the pad is suppressed and the side leakage of the body fluid can be surely prevented.

As illustrated in FIG. 1, the inclined embosses 13 are a pair of embossed lines in the lateral direction wherein each extends from the outer end portion of the longitudinal direction emboss 12 and is formed to be inclined toward a center side in the width direction of the incontinence pad 1. The inclined embosses 13 are provided to guide the flow of the body fluid that diffuses toward the outer side of the pad along the longitudinal direction embosses 12 toward inside of the width direction of the pad. For the example illustrated in FIG. 1, the inclined embosses 13 are constituted of first inclined embosses 13A that extend from outer end portions of the first longitudinal direction embosses 12A, and second inclined embosses 13B that extend from outer end portions of the second longitudinal direction embosses 12B, respectively.

Figure 5:
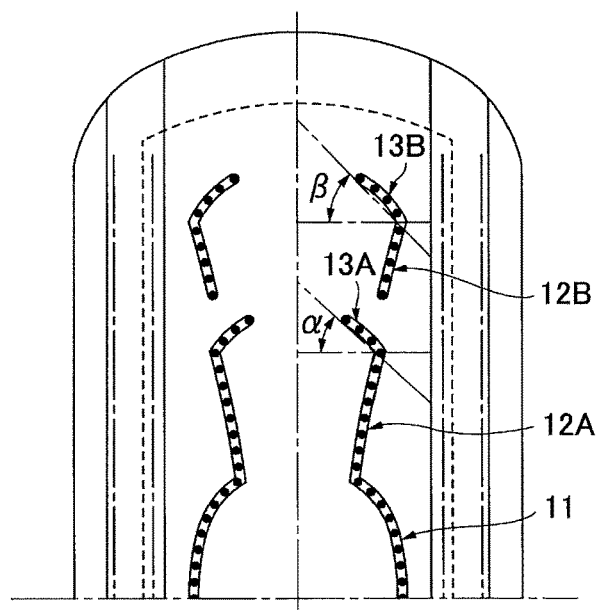
FIG. 5 is a plan view of the incontinence pad 1.

It is preferable that each of the inclined embosses 13 is constituted of a straight line or a curve. In particular, as illustrated in FIG. 5, in order to easily guide the body fluid that diffuses along the longitudinal direction emboss 12 toward inside, it is desirable that each of the inclined embosses 13 is configured by an arc-shaped curve that protrudes outward in the longitudinal direction of the pad.

Front end portions of the right and left inclined embosses 13, 13 are spaced apart from each other in the width direction, and a dividing part 18, at which an emboss is not formed, is provided at a center portion in the width direction of the pad. In other words, the inclined embosses 13 extend from outer end portions of the longitudinal direction embosses 12, that are spaced apart from each other in the lateral direction, toward a center side in the width direction of the pad to a middle portion in the width direction of the pad. By providing the dividing part 18, suppression of the diffusion of the body fluid that diffuses in the absorbent body in the longitudinal direction by the embosses 10 can be prevented.

It is preferable that an inner side end portion of the inclined emboss 13 in the width direction of the pad, when the longitudinal direction emboss 12 is placed at its outer side, is positioned at an inner side in the width direction of the pad, of an inner side end portion of the respective longitudinal direction emboss 12. With this, when the body fluid that is guided toward inner side of the pad along the inclined emboss 13 is diffused at the outer side in the longitudinal direction of the pad, the body fluid can be diffused by the longitudinal direction emboss 12 that is placed at the outer side outward in the width direction of the pad to suppress side leakage.

The first inclined emboss 13A and the second longitudinal direction emboss 12B that is formed at the outer side thereof may be provided, as illustrated in FIG. 1, such that the longitudinal direction emboss 12B is provided to be spaced apart from the outer end portion of the inclined emboss 13A in the longitudinal direction of the pad without having an overlapping area in the width direction of the pad. Alternatively, the first inclined emboss 13A and the second longitudinal direction emboss 12B may be provided such that the longitudinal direction emboss 12B is provided from a position of the outer end portion of the inclined emboss 13A without having an overlapping area in the width direction of the pad. Alternatively, the first inclined emboss 13A and the second longitudinal direction emboss 12B may be provided such that the inclined emboss 13 and the longitudinal direction emboss 12 have an overlapping area in the width direction of the pad within a range that they are not connected with each other.

As illustrated in FIG. 5, the first inclined emboss 13A is provided such that an angle α with respect to a width direction line of the incontinence pad 1 is less than or equal to 45°, preferably, within 20° to 45°. With this, the body fluid that flows in the first longitudinal direction emboss 12A is surely guided inward, and absorption of the body fluid guided inward by the absorbent body can be ensured. Further, the body fluid that diffuses in the absorbent body can be diffused inward. When the first inclined emboss 13A is constituted by a curve, an angle between a line that connects a connecting portion with the first longitudinal direction emboss 12A and a front end portion with respect to the width direction line may be taken as the angle α.

As illustrated in FIG. 5, the second inclined emboss 13B is provided such that an angle β with respect to the width direction line of the incontinence pad 1 is less than or equal to 60°, preferably, greater than or equal to the angle α and less than or equal to 60°. With this, larger dimension can be ensured for the area surrounded by the second longitudinal direction emboss 12B and the second inclined emboss 13B, and the body fluid that passes over the first longitudinal direction emboss 12A and moves to the outer side can be surely absorbed in the absorbent body.

Figure 6:
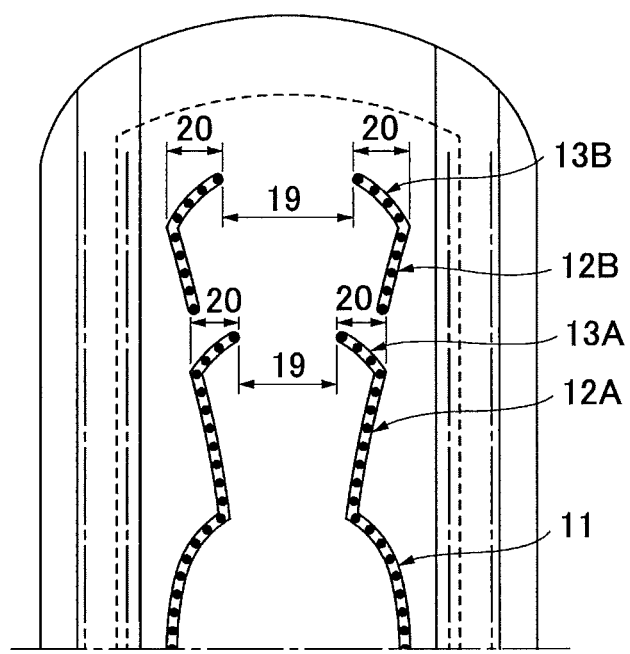
FIG. 6 is a plan view of the incontinence pad 1.

As illustrated in FIG. 6, the width 19 of the dividing part 18 between the right and left inclined embosses 13, 13 is 1 to 3 times, preferably, within 1.5 to 2.5 times, of an inclined portion width 20, which is the length of the inclined emboss 13 in the width direction of the pad. By making the distance 19 to be greater than the inclined portion width 20, a diffusion path of the body fluid diffusing in the absorbent body in the longitudinal direction of the pad can be retained with a sufficient width, the natural diffusion of the body fluid toward front and rear directions of the absorbent body is not blocked, the body fluid does not trapped between the body fluid expelling part embosses 11, 11, and the stickiness can be suppressed.

The groove widths of the body fluid expelling part emboss 11, the longitudinal direction emboss 12 and the inclined emboss 13 may be the same or may be different. For the example illustrated in FIG. 1 or the like, it is illustrated that the groove widths of all of the embosses 11, 12 and 13 are the same. Alternatively, as will be described later in the second embodiment, those may be formed to have different groove widths, such as making the groove width of the inclined emboss 13 larger than the groove width of the longitudinal direction emboss 12, or the like. The "groove width" means a width of a bottom portion in a cross-section traversing the emboss. When the highly compressed portion is provided at an emboss bottom portion of a low compressed portion as this example, a width of the low compressed portion is adopted.

It is preferable that each of the embosses 10 is symmetrically positioned in the front and the rear directions with respect to a center position of the body fluid expelling part emboss 11, the pad width direction center line CW for the incontinence pad 1 illustrated in FIG. 3. In particular, by symmetrically positioning the inclined embosses 13 in the front and rear directions, the absorbed amount of the body fluid can be accurately recognized based on the diffusion status of the body fluid after being used.

In the incontinence pad 1 having the above described structure, the emboss 10 is constituted of the body fluid expelling part emboss 11, the longitudinal direction embosses 12 formed along the longitudinal direction of the pad at the front and the rear of the body fluid expelling part emboss 11, respectively, and the inclined embosses 13 extending from the outer end portions of the longitudinal direction embosses 12 and being inclined toward a center side in the width direction of the pad, respectively. With this, by using the inclined embosses 13 as a scale, the degree of diffusion of the body fluid in the absorbent body can be recognized just by viewing the pad surface after being used, and the diffusion status of the body fluid can be used as a guidepost for selecting the size of the pad thereafter.

At this time, according to the incontinence pad 1, as the dividing part 18 for spacing apart the end portions of the right and left inclined embosses 13 in the width direction is provided, limitation of the diffusion of the body fluid in the absorbent body by the embosses 10 in the front and rear directions can be prevented, and an accurate diffusion status of the body fluid in the absorbent body can be recognized. Further, as the diffusion of the body fluid is not suppressed, the body fluid does not stay near the body fluid expelling part, and discomfort due to the stickiness can be eased.

Figure 7:
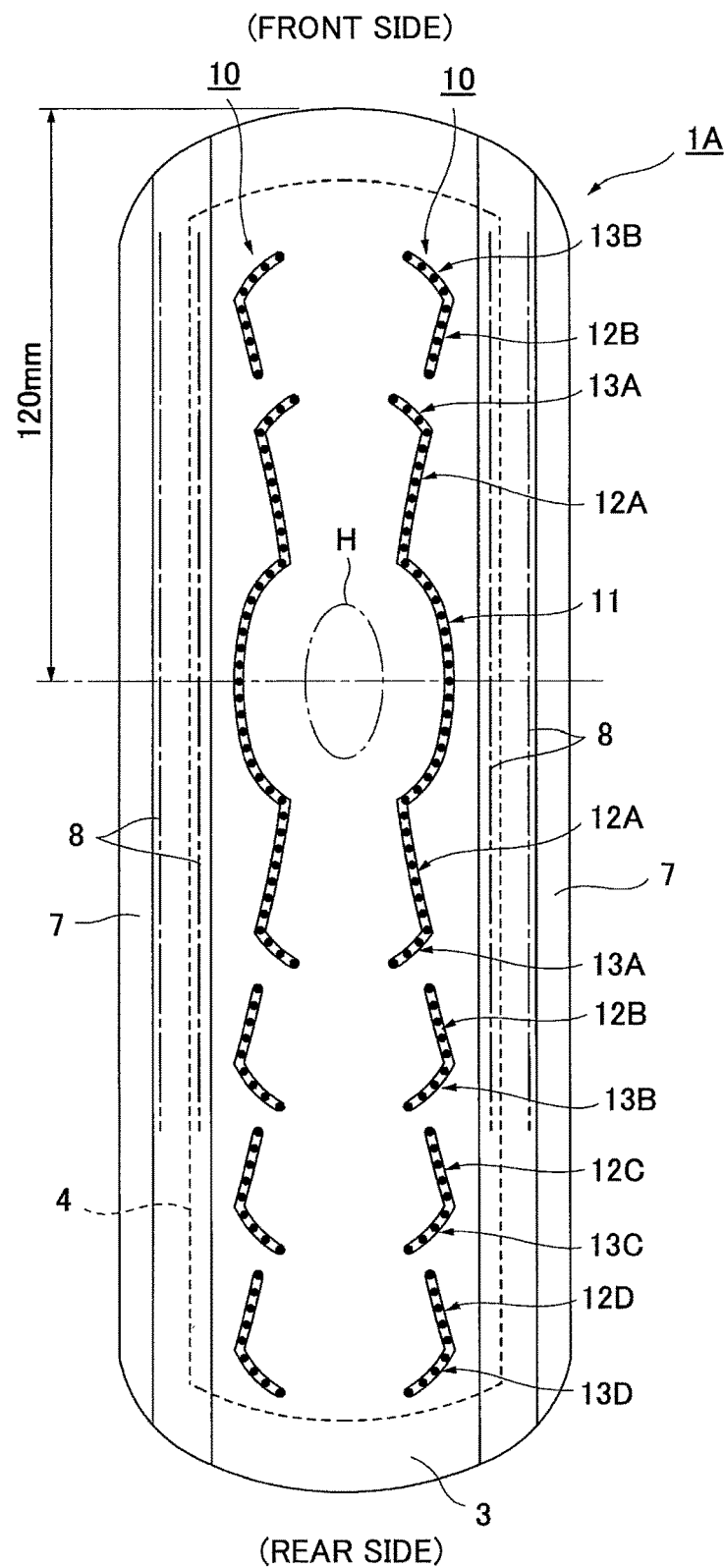
FIG. 7 is a plan view of an incontinence pad 1A of another embodiment.

Next, as an incontinence pad 1A of another embodiment, as illustrated in FIG. 7, a structure is described in which the length of a pad rear side is longer than the length of a pad front side with respect to a center portion of the body fluid expelling part emboss 11 (center portion of the body fluid expelling area H) to cover a larger area at a backside in order to prevent backside leakage that flows in a groove at backside. In such a case, it is preferable that the body fluid expelling part embosses 11 are provided such that a center portion of the body fluid expelling part embosses 11 in the longitudinal direction of the pad is positioned at about 120 mm from a front end of the pad. By providing the body fluid expelling part embosses 11 at this position, when attaching to contact the body fluid expelling part by targeting the center portion of the body fluid expelling part embosses 11, the incontinence pad can be attached without the occurrence of discomfort due to excessive length of the front of the pad.

While it is preferable that each of the embosses 10 is symmetrically provided in the front and rear directions with respect to a center position of the body fluid expelling part embosses 11, when the length at the rear side of the pad is long, as in this example, the number of the longitudinal direction embosses 12 and the inclined embosses 13 may not necessarily be equal at the front side and the rear side. For example, the number of the longitudinal direction embosses 12 and the inclined embosses 13 may be greater at the rear side than that at the front side. For the illustrated example, two pairs of each of the longitudinal direction embosses 12 and the inclined embosses 13 are provided (12A and 12B, and 13A and 13B) at the pad front side, while four pairs of each of the longitudinal direction embosses 12 and the inclined embosses 13 (12A to 12D and 13A to 13D) are provided at the pad rear side.

Figure 8:
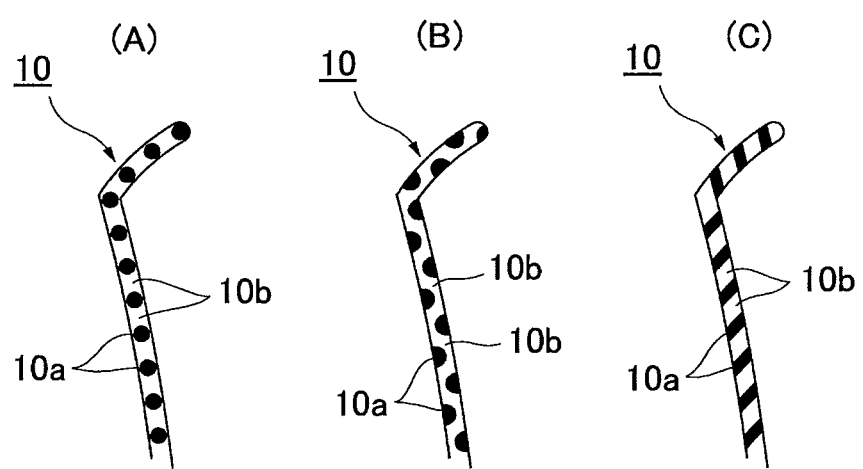
FIG. 8 is a plan view of an emboss 10.

Here, although a groove bottom portion of the emboss 10 may be a flat pattern obtained by compressing it at a constant depth, as illustrated in FIG. 8, it is preferable that highly compressed portions 10a (doted portions) and low compressed portions 10b (white portions) with various patterns are provided at a bottom portion of the embossed groove. FIG. 8-(A) illustrates a structure in which circular highly compressed portions 10a are provided at a center portion of a groove bottom surface with predetermined spaces therebetween, FIG. 8-(B) illustrates a structure in which semi-circular highly compressed portions 10a are alternately provided at both side portions of the groove bottom surface, and FIG. 8-(C) illustrates a structure in which oblique highly compressed portions 10a are provided along the groove bottom surface. By providing the highly compressed portions 10a in various embodiments as such, flow of the body fluid along the embossed groove can be suppressed, the body fluid can be easily penetrated in the absorbent body, and the shape retention of the embossed groove can be increased.

Meanwhile, by providing coloring design to either of or two or more sheet materials including the liquid permeable topsheet 3, the encapsulating sheet 5 and the second sheet provided in accordance with necessity, at the embossed groove bottom portion or a range surrounded by the emboss, with the combination of the emboss 10, the attachment position or the scale function may be furthermore recognizable. For example, by coloring the embossed groove bottom portions of the first longitudinal direction emboss 12A and the first inclined emboss 13A, and the embossed groove bottom portions of the second longitudinal direction emboss 12B and the second inclined emboss 13B in different colors, the diffusion range of the body fluid can be clearly recognizable. Further, by coating a material that shows color reaction upon contacting the body fluid on a bottom surface or the inclined embosses 13 or the like, it is possible to increase visibility of the diffusion of the body fluid as the diffusion of the body fluid can be recognized by the range at which the color is changed.

Second Embodiment

Figure 9:
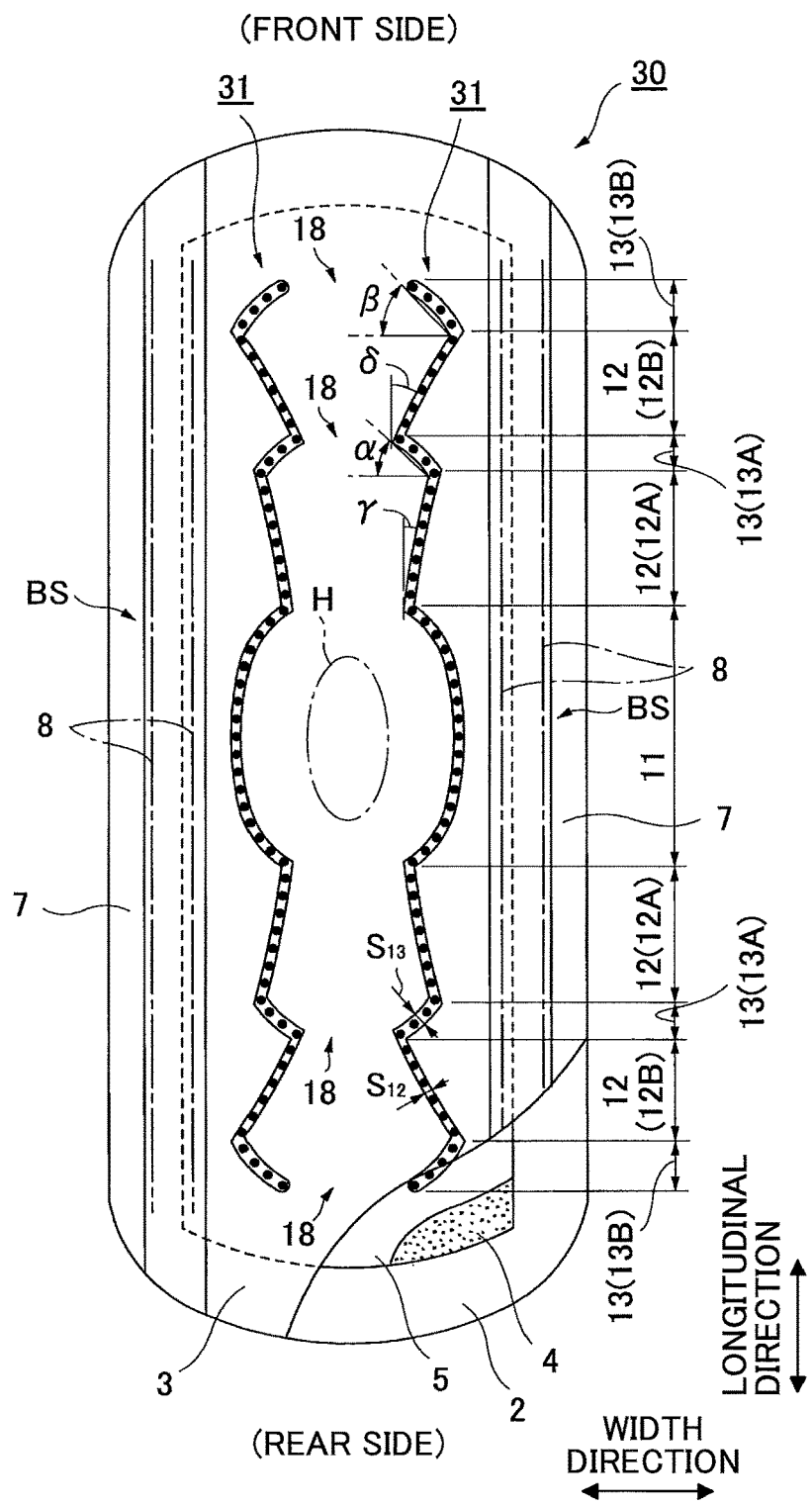
FIG. 9 is a partially broken development view of an incontinence pad 30 of a second embodiment.

Next, an incontinence pad 30 of the second embodiment of the invention is described with reference to FIG. 9. In the following, only parts that differ from those of the above described incontinence pad 1 of the first embodiment are described, and those that are not specifically described are the same as those of the above described incontinence pad 1 of the first embodiment.

In the incontinence pad 30 of the second embodiment, as a pair of embosses 31 in the lateral direction formed at a surface side of the liquid permeable topsheet 3, two pairs of the longitudinal direction embosss 12 are formed at each of front and rear of the body fluid expelling part embosses 11. For the example illustrated in FIG. 9, two pairs of the longitudinal direction embosses 12 (the first longitudinal direction emboss 12A and the second longitudinal direction emboss 12B from inner side in this order) are formed at each of front and rear of the body fluid expelling part embosses 11.

Similar to the above described incontinence pad 1 of the first embodiment, the longitudinal direction emboss (first longitudinal direction emboss 12A) that is adjacent to the body fluid expelling part emboss 11 connects to the body fluid expelling part emboss 11. In other words, the outer end portion of the body fluid expelling part emboss 11 in the longitudinal direction of the pad is connected to the inner side end portion of the first longitudinal direction emboss 12A in the longitudinal direction of the pad so that a continuous embossed groove is formed.

Further, similar to the above described incontinence pad 1 of the first embodiment, the inclined embosses 13 are formed at the outer end portions of the longitudinal direction embosses 12, respectively. For the illustrated example, the first inclined emboss 13A is formed at the outer end portion of the first longitudinal direction emboss 12A, and the second inclined emboss 13B is formed at the outer end portion of the second longitudinal direction emboss 12B. In other words, the outer end portion of the first longitudinal direction emboss 12A in the longitudinal direction of the pad is connected to the outer end portion of the first inclined emboss 13A in the width direction of the pad so that a continuous embossed groove is formed. Further, the outer end portion of the second longitudinal direction emboss 12B in the longitudinal direction of the pad is connected to the outer end portion of the second inclined emboss 13B in the width direction of the pad so that a continuous embossed groove is formed.

Then, according to the incontinence pad 30 of the second embodiment, the longitudinal direction emboss 12 that is adjacent to the inclined emboss 13 at its outer side is connected to this inclined emboss 13. For the example illustrated in FIG. 9, the second longitudinal direction emboss 12B that is adjacent to the first inclined emboss 13A at the outer side is connected to the inner side end portion of the first inclined emboss 13A. In other words, the inner side end portion of the first inclined emboss 13A in the width direction of the pad connects to the inner side end portion of the second longitudinal direction emboss 12B in the longitudinal direction of the pad so that a continuous embossed groove is formed.

As illustrated in FIG. 1 and the like, the emboss 10 is formed by separated lines spaced apart between the first inclined emboss 13A and the adjacent second longitudinal direction emboss 12B at the outer side in the incontinence pad 1 of the first embodiment. However, according to the incontinence pad 30 of the second embodiment, as illustrated in FIG. 9, the emboss 31 is formed by a continuous line in which the body fluid expelling part emboss 11, the longitudinal direction embosses 12 and the inclined embosses 13 are continuously formed.

Figure 10:
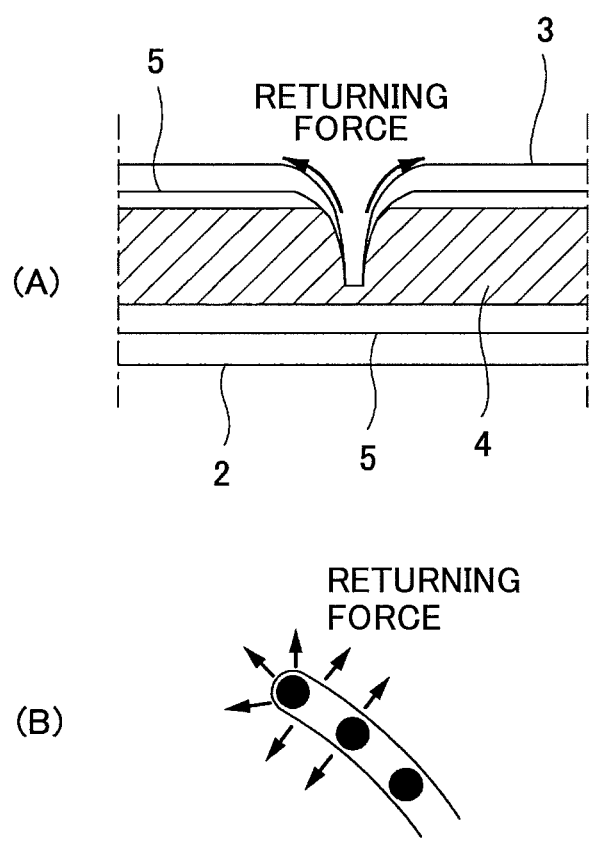
FIG. 10 illustrates a returning force of an emboss, wherein (A) is a cross-sectional view and (B) is a plan view.

When the emboss is formed from a front surface side of the liquid permeable topsheet 3, as illustrated in FIG. 10-(A), a surface material such as the liquid permeable topsheet 3 or the like is strongly pulled by this emboss, and a returning force for returning the surface material is generated. This returning force causes a floating (detachment) of the emboss in which the surface material floats from the absorbent body, and there are problems that the appearance of the emboss becomes bad and also the effect of the emboss is reduced. In particular, as FIG. 10-(B), at an end portion of the emboss, the above described returning force is applied in a direction of the end portion of the emboss in addition to both side directions of the emboss. Thus, it is assumed that a floating is generated from this end portion and this will gradually expand. Thus, if the emboss is formed by separated lines, a large number of end portions are formed at the separated portions, and the floating of the emboss is generated therefrom.

Thus, as described above, the emboss 31 is formed by the continuous line in the longitudinal direction of the incontinence pad 30 of the second embodiment so that the fewest number of end portions of the emboss are formed.

Further, according to the incontinence pad 30 of the second embodiment, as the second longitudinal direction emboss 12B is connected to the inner side end portion of the first inclined emboss 13A, the function of the first inclined emboss 13A as a scale is not lost and the degree of diffusion of the body fluid in the absorbent body can be visible.

However, by forming the emboss 31 by the continuous line, the body fluid can easily diffuse in the longitudinal direction of the incontinence pad 30 along the emboss 31, and there is a possibility that influences on the recognition of the diffusion status of the body fluid absorbed in the absorbent body, which is the original purpose of the present incontinence pad, the following means are preferably adopted. These means may be used singularly or in combination. Further, these means may be adopted for the above described incontinence pad 1 of the first embodiment.

First, as a first means, as described above, the longitudinal direction emboss 12 may be formed to have an inclined angle such that its outer side in the longitudinal direction is inclined outward in the width direction with respect to a longitudinal direction line of the incontinence pad 30 and the inclined angle of the second longitudinal direction emboss 12B that is provided relatively outer side may be set to be larger than the inclined angle of the adjacent first longitudinal direction emboss 12A that is at an inner side thereof. Specifically, as illustrated in FIG. 9, when an angle between the first longitudinal direction emboss 12A and the longitudinal direction line of the pad is referred to as an inclined angle $\gamma$ of the first longitudinal direction emboss 12A, and an angle between the second longitudinal direction emboss 12B and the longitudinal direction line of the pad is referred to as an inclined angle $\delta$ of the second longitudinal direction emboss 12B, these are formed as a relation of $\gamma<\delta$. It is preferable that the inclined angle $\delta$ is about 15 to 20° greater than the inclined angle $\gamma$. Here, the inclined angle $\gamma$ of the first longitudinal direction emboss 12A is less than or equal to 20°, preferably, within 5° to 15°, and more preferably, within 8° to 12°, and the inclined angle $\delta$ of the second longitudinal direction emboss 12B is less than or equal to 37°, preferably, within 22° to 32°, and more preferably, within 25° to 29°.

By setting the inclined angle to be larger at the outer side in the longitudinal direction of the pad, even when the emboss that continuously extends in the longitudinal direction is formed as the incontinence pad 30 of the second embodiment, the diffusion of the body fluid in the longitudinal direction of the pad along the emboss can be suppressed in particular at the outer side in the longitudinal direction of the pad, at which the inclined angle is large. Thus, the diffusion status of the body fluid absorbed in the absorbent body can be easily recognized.

Next, as a second means, the groove width of the inclined emboss 13 may be set greater than the groove width of the longitudinal direction emboss 12. Specifically, as illustrated in FIG. 9, assuming that the groove width of the inclined emboss 13 as "$S_{13}$", and the groove width of the longitudinal direction emboss 12 as "$S_{12}$", they are formed to satisfy $S_{13}>S_{12}$. The groove width $S_{13}$ of the inclined emboss 13 is 1.2 to 2.0 times, preferably, 1.4 to 1.7 times, of the groove width $S_{12}$ of the longitudinal direction emboss 12.

By setting the groove width of the inclined emboss 13 to be larger, the body fluid that flows along the longitudinal direction emboss 12 is temporarily trapped in the inclined emboss 13 and the diffusion of the body fluid along the embossed groove is suppressed. The diffusion status of the body fluid absorbed in the absorbent body can be easily recognized.

Other Embodiments

Although the emboss 10 is constituted of the body fluid expelling part emboss 11, the longitudinal direction embosses 12 and the inclined embosses 13 in the above embodiment, in addition, a predetermined emboss may be arbitrarily provided without departing from the spirit and scope of the invention.

NUMERALS 1, 30 incontinence pad;
2 liquid impermeable backsheet;
3 liquid permeable topsheet;
4 absorbent body;
5 encapsulating sheet;
7 side non-woven-fabric;
8 threadlike elastic stretchable member;
10, 31 emboss;
11 body fluid expelling part emboss;
12 longitudinal direction emboss;
12A first longitudinal direction emboss;
12B second longitudinal direction emboss;
13 inclined emboss;
13A first inclined emboss;
13B second inclined emboss;
14 arc-shaped curve;
15 narrowest portion;
16 maximum protruding portion;
18 dividing part.

What is claimed is:
1. An absorbent article comprising:
an absorbent body provided between a liquid permeable topsheet and a backsheet; and
a pair of embosses formed at both sides of a surface side of the liquid permeable topsheet,
wherein each of the embosses includes
a body fluid expelling part emboss formed at an area corresponding to a body fluid expelling part along a longitudinal direction of the absorbent article, and is constituted of a shaped line protruding outward in a width direction of the absorbent article, longitudinal direction embosses formed at the front and the rear of the body fluid expelling part emboss along the longitudinal direction of the absorbent article, respectively, and inclined embosses extending from outer end portions of the longitudinal direction embosses, respectively, and being inclined, from the outer end portions of the longitudinal direction embosses toward outer sides relative to a center region in the longitudinal direction, respectively, toward a center side in the width direction of the absorbent article, and wherein end portions of the right and left inclined embosses are spaced apart from each other in the width direction.

2. The absorbent article according to claim 1, wherein two or more pairs of the longitudinal direction embosses are formed at each of front and rear of the pair of body fluid expelling part embosses with spaced apart from each other in the longitudinal direction, wherein the pairs of longitudinal direction embosses adjacent to the pair of body fluid expelling part embosses are formed to be directly connected to the respective body fluid expelling part embosses, and wherein the inclined emboss is formed at the outer end portion of each of the longitudinal direction embosses.

3. The absorbent article according to claim 2, wherein in each of the embosses, each of the longitudinal direction embosses, that is provided relatively outer side with respect to the center region in the longitudinal direction, is provided at a position that does not match an extension line extending from the adjacent longitudinal direction emboss that is at an inner side thereof in the longitudinal direction.

4. The absorbent article according to claim 2, wherein in each of the embosses, each of the longitudinal direction embosses, that is provided relatively outer side with respect to the center region in the longitudinal direction, is provided inside of an extension line extending from the adjacent longitudinal direction emboss that is at an inner side thereof in the longitudinal direction.

5. The absorbent article according to claim 2, wherein, among the inclined embosses, each of the inclined embosses formed nearest to the body fluid expelling part emboss is formed such that an angle α, with respect to a width direction line of the absorbent article, is less than or equal to 45°, and each of the inclined embosses formed further outer side is formed such that an angle, with respect to the width direction line of the absorbent article, is less than or equal to 60°.

6. The absorbent article according to claim 2, wherein each of the longitudinal direction embosses is formed to be inclined, toward its outer side relative to the center region in the longitudinal direction, outward in the width direction with respect to a longitudinal direction line of the absorbent article, and wherein in each of the embosses, an inclined angle of each of the longitudinal direction embosses provided relatively outer side with respect to the center region in the longitudinal direction is set to be larger than an inclined angle of the adjacent longitudinal direction emboss at an inner side thereof with respect to the center region in the longitudinal direction.

7. The absorbent article according to claim 1, wherein two or more pairs of the longitudinal direction embosses are formed at each of front and rear of the pair of body fluid expelling part embosses, wherein the pairs of longitudinal direction embosses adjacent to the pair of body fluid expelling part embosses are formed to be directly connected to the respective body fluid expelling part embosses, wherein the inclined emboss is formed at the outer end portion of each of the longitudinal direction embosses, and wherein each of the longitudinal direction embosses adjacent to the inclined emboss at its outer side relative to the center region in the longitudinal direction is directly connected to the respective inclined emboss.

8. The absorbent article according to claim 1, wherein each of the longitudinal direction embosses adjacent to the body fluid expelling part emboss is formed along a single arc-shaped curve that protrudes inward in the width direction of the absorbent article, and wherein a position of narrowest portions, at which the distance between the right and left arc-shaped curves becomes the minimum, and a position of maximum protruding portions, at which an outward protruding width in the width direction of the right and left body fluid expelling part embosses, match or are in proximity to each other.

9. The absorbent article according to claim 1, wherein the distance between end portions of the right and left inclined embosses is one to three times of the length of the respective inclined emboss in the width direction of the absorbent article.

10. The absorbent article according to claim 1, wherein the groove width of each of the inclined embosses is wider than the groove width of each of the longitudinal direction embosses.

11. The absorbent article according to claim 1, wherein the body fluid expelling part is formed by a single curve.

12. The absorbent article according to claim 1, wherein in each of the embosses, the longitudinal direction embosses are directly connected to the front and the rear of the body fluid expelling part emboss, respectively, and the inclined embosses are directly connected to the outer end portions of the longitudinal direction embosses, respectively.

13. The absorbent article according to claim 1, wherein the body fluid expelling part emboss is formed at the center region in the longitudinal direction of the absorbent article.

* * * * *